(12) United States Patent
Weitschies et al.

(10) Patent No.: US 6,485,985 B1
(45) Date of Patent: *Nov. 26, 2002

(54) PROCESSES AND COMPOUNDS FOR MAGNETORELAXOMETRIC DETECTION OF ANALYTES AND THEIR USE

(75) Inventors: Werner Weitschies, Berlin (DE); Roman Kottiz, Berlin (DE); Lucz Trahms, Berlin (DE); Thomas Bunte, Berlin (DE)

(73) Assignee: Schering Aktiengesellschaft, Berlin (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/389,223

(22) Filed: Sep. 3, 1999

Related U.S. Application Data

(63) Continuation of application No. 08/875,418, filed on Feb. 23, 1998, now Pat. No. 6,027,946.

(51) Int. Cl.⁷ .................. G01N 33/553; G01N 33/566; G01N 25/18

(52) U.S. Cl. ................ 436/526; 436/501; 436/149; 436/173; 436/806; 435/7.1

(58) Field of Search ................ 436/526, 501, 436/149, 173, 806, 518, 523, 524, 525, 544, 64, 65; 435/7.1, 4, 7.2, 7.21, 7.22, 7.23, 7.4

(56) References Cited

U.S. PATENT DOCUMENTS

| 5,164,297 A | 11/1992 | Josephson et al. |
| 6,027,946 A | * 2/2000 | Weitschies et al. ......... 436/526 |

FOREIGN PATENT DOCUMENTS

| DE | 4309333 | 9/1994 |
| WO | 91/15243 | 10/1991 |

* cited by examiner

*Primary Examiner*—Padmashri Ponnaluri
(74) *Attorney, Agent, or Firm*—Millen, White, Zelano & Branigan, P.C.

(57) ABSTRACT

A process for magnetorelaxometric quantitative detection of analytes in the liquid and solid phases, compounds for magnetorelaxometric detection, and their use in analysis and immunomagnetography is described.

12 Claims, 4 Drawing Sheets

PROCESSES AND COMPOUNDS FOR MAGNETORELAXOMETRIC DETECTION OF ANALYTES AND THEIR USE

This application is a continuation of U.S. application Ser. No. 08/875,418, filed on Feb. 23, 1998, which has now issued as U.S. Pat. No. 6,027,946 on Feb. 22, 2000.

This invention relates to processes for magnetorelaxometric qualitative and/or quantitative detection of analytes in the liquid and solid phases, compounds for magnetorelaxometric detection, and their use in analysis and immunomagnetography.

It is already known that immunoscintigraphy makes it possible to detect pathological structures in vivo with the aid of radiolabeled structure-specific substances, which are also referred to below as markers. To this end, antibodies that are labeled with γ-rays or antibody fragments are usually used. In addition, other structure-specific substances, such as, e.g., peptides or oligonucleic or polynucleic acids are also used or are being researched. The portion of specifically bound radioactivity is, however, generally small in all these processes. Consequently, in the case of these studies, the levels of markers that are not specifically bound and thus circulate in the blood or accumulate in organs such as the liver, kidney, efferent urinary passages, or bladder are very high. In many cases, this high background radiation impedes adequate detection of pathological structures. In EP 0251494, in Panchapakesan et al., 1992 Immunol. Cell Biol. 70:295 and in Ziegler et al., 1991, New England Journal of Medicine 324:430, reference is therefore made to ways of improving immunoscintigraphy. The goal of most of the processes is to accelerate the elimination of radioactivity that is not specifically bound.

In addition, the use of antibodies that are conjugated with paramagnetic or superparamagnetic substances or antibody fragments for locating pathological structures in vivo has been proposed on various occasions. To date, nuclear spin tomography or the magnetometry that is based on changes in susceptibility (WO93/05818 and WO91/15243) have been considered as detection processes for such labeled antibodies. In the case of these detection processes, the problem of the variable portion of the signal owing to unbound portions of the marker as well as owing to natural variations in the susceptibility and relaxivity of the tissue also remains present. In addition, the methods often are not sensitive enough to be able to detect just small amounts of specifically bound markers.

A process that makes it possible to detect only the portion of bound markers and thus is not influenced by the extent of the unbound markers is not known, however.

One of the objects of this invention is therefore to develop new processes and substances that are superior to the above-mentioned prior art and that make it possible to detect the retention site without using radioactive substances and the extent of the bound markers without the influence of markers that circulate in the blood.

In addition, it is also already known that quantitative immunoassays as well as other binding assays (e.g., receptor binding assays) make it possible to determine a very large number of substances that can also be of biological relevance in samples of varying composition. Generally, however, only one parameter per sample in an assay is determined in this way. An existing survey of the various processes is: T. Chard; An Introduction to Radioimmunoassay and Related Techniques: Laboratory Techniques in Biochemistry and Molecular Biology, 4th ed., Elsevier Science Publishers, Amsterdam (1990). The basis of all binding assays is the high detection sensitivity of compounds that are labeled with isotopes or by some other means with the high specificity of ligand-receptor reactions.

The known assay processes have the following drawbacks, however:

1. The processes for simultaneous determination of various analytes within the same sample are based on the binding of various radio-, fluorescence- or enzymologically-labeled probes to the analytes. In this case, the unbound or bound activity of the probes for quantitative determination of the analyte is generally measured after subsequent separation and washing. In this case, the amount of usable different probe labels is very limited. Thus, for example, in the case of different radioisotopes as probe labels, so-called overlapping phenomena occur which lead to a rapid loss of the quantitative accuracy of individual signals. The combination of various enzymes as probe labels causes comparable problems, whereby the feasibility here is further hampered by the necessary search for reaction conditions that allow the simultaneous determination of enzyme reactions in a system.

2. The sensitivity of the process is limited by, for example, non-specific interactions between matrix and probe, or else by limited labeling capability on the part of the probe (low specific activity).

3. The successful implementation of the process often requires that the sample material obtained be worked up (e.g., production of serum or plasma from whole blood, extraction of samples with organic solvents, concentration of the analyte using chromatographic processes, etc.).

4. For successful implementation of the processes, separation and washing steps, which are used in the separation of bound and unbound receptors or ligand, are essential in most cases.

5. To carry out radioimmunoassays, the use of radiating nuclides, which are costly and complicated to handle, is necessary.

6. In practice, the storage of previously used markers often causes problems since they are either unstable (radioimmunoassays) and must therefore constantly be made up fresh or else react in a sensitive manner to environmental influences.

Another object of this invention is therefore to develop novel, economical processes and substances that overcome the drawbacks of the above-mentioned prior art.

First processes are now described that overcome the drawbacks of the known processes for implementing immunoassays or other binding assays.

The processes according to the invention are based on the use of colloidal ferromagnetic or ferrimagnetic substances, also referred to below as magnetic labeling, which are combined with substances to be identified—also referred to below as analytes—or structure-specific substances. Such combinations, according to the invention, of magnetic labelings with analytes or structure-specific substances, which are described in more detail in this patent, are also referred to below as magnetic markers. Through the use of the term colloidal substances or colloidal particles, both the range of sizes of the particles or substances in the size range of colloids, i.e., the range of 1 nm up to about 1000 nm, and their use as a dispersed phase in a suitable dispersion medium, which is aqueous in most cases, is described. To ensure improved storability and transportability, the colloidal substances or particles can also be present in dried form or frozen; while measurements are being made, however, they are present in the liquid phase in the dispersed state.

In addition, the processes are based on special measuring techniques, which make it possible to determine the relaxation of magnetization after the magnetic labeling or the magnetic markers are magnetized. Such measuring processes according to the invention, which are described in more detail in this patent, are also referred to below as magnet-relaxometry or magnetorelaxometry or magnet-relaxometric detection.

An important principle of the invention is that after an external magnetizing field is turned off, the magnetization of freely movable ferromagnetic or ferrimagnetic colloidal particles relaxes by two different mechanisms:

i) Turning of the whole colloidal particle inside the surrounding liquid, whereby the time constant depends on the hydrodynamic diameter of the particles including the shell, the viscosity of the carrier liquid, and temperature, which mainly reflects parameters of the environs of the particles; this mechanism is also referred to below as Brownian relaxation or extrinsic superparamagnetism, and ii) Turning of the internal magnetizing vector inside the colloidal particles, whereby the time constant depends in a very sensitive manner on material and shape (the anisotropy constants of the particle material used), volume and the temperature of the particles used. These are basically intrinsic parameters of the particles; this mechanism is also referred to below as Néelian relaxation or intrinsic superparamagnetism.

The object according to the invention is achieved by virtue of the fact that in immunoassays or other binding assays, ferromagnetic or ferrimagnetic colloidal particles, whose Brownian relaxation proceeds faster than the Néelian relaxation under measurement conditions in the unbound state, are used as magnetic labeling to be identified. Owing to the change in the predominant relaxation mechanism or to the scaling-up of the particle volume, which is caused by the binding, the use of such ferromagnetic or ferrimagnetic colloidal particles then makes it possible to determine specifically the portion of bound magnetic markers in addition to the unbound magnetic labels that are simultaneously present in the measuring sample.

By the use of sensitive measuring processes, in the case of the procedure according to the invention, ultrahighly sensitive binding-specific immunoassays or other binding assays which can be performed both in the liquid phase and in the solid phase can be set up using ferromagnetic or ferrimagnetic colloidal particles. As an especially sensitive measuring process, after the sample is magnetized in a magnetizing field and after the field is turned off, the relaxation of the magnetization can be determined with the aid of highly sensitive magnetic field detectors (such as, e.g., superconducting quantum interference devices (SQUIDs), induction coils, flux gate magnetometers, giant magnetoresistance sensors, or magnetoresistive converters), or the complex susceptibility of the sample can be determined as a function of frequency.

The process for magnet-relaxometric quantitative detection of analytes in the liquid and solid phases is also characterized according to the invention in that the structure-specific substances that bind the analytes first i) are labeled with ferromagnetic or ferromagnetic colloidal particles and then ii) these magnetically labeled structure-specific substances are used in a liquid or immobilized sample to be measured, the sample to be measured is magnetized with the aid of a magnetic field that is applied from the outside and, after the outside field is turned off, the relaxation of the magnetization of the magnetic markers is measured with the aid of magnetic field sensors.

The process for magnet-relaxometric quantitative detection of analytes in the liquid and solid phases according to the invention can also be carried out in such a way that analytes first i) are labeled with ferrimagnetic or ferromagnetic colloidal particles and then ii) these magnetically labeled analytes are used in a liquid or immobilized sample to be measured, the substances that specifically bind the analytes are added, and the sample to be measured is magnetized with the aid of a magnetic field that is applied from the outside and, after the outside field is turned off, the relaxation of the magnetization of the magnetic markers is measured with the aid of magnetic field sensors.

In both above-named cases, the measurement of the complex susceptibility of the magnetic labeling or the magnetic marker that is altered by the binding can also be used as a function of frequency for analysis.

The discrimination between bound and unbound markers, which previously could be done only in exceptional cases, is made possible by the use of their different relaxation mechanisms or the influence of the relaxation time of the magnetic marker that is caused by the binding.

Solid-phase-bound analytes can be identified according to the invention especially by the structure-specific substances that bind the analytes first i) being labeled with the ferrimagnetic or ferromagnetic colloidal particles that relax in the time range of the measurement, whereby the ferrimagnetic or ferromagnetic colloidal particles are selected in such a way that under the measurement conditions, the Brownian relaxation has a shorter relaxation time than the Néelian relaxation and then ii) these magnetically labeled substances being used in an immobilized sample to be measured, and the sample to be measured is magnetized with the aid of a magnetic field of suitable intensity that is applied from the outside and, after the outside field is turned off, the relaxation of the magnetization of the magnetic markers is measured with the aid of magnetic field sensors, whereby the different relaxation behaviors of solid-phase-bound and unbound magnetic markers are used for analysis. As a measurement variable, the complex susceptibility of the samples can also be determined as a function of frequency.

Also in this case, it is possible to combine the analytes to be identified, instead of structure-specific substances, with the magnetic labelings.

In the liquid phase, analytes according to the invention can be detected especially by the structure-specific substances that bind the analytes first i) being labeled with ferrimagnetic or ferromagnetic colloidal particles, whereby the ferrimagnetic or ferromagnetic colloidal particles are selected in such a way that under the measurement conditions the Brownian relaxation has a shorter relaxation time than the Néelian relaxation and then ii) these magnetically labeled substances being used in a sample to be measured, and the sample to be measured is magnetized with the aid of a magnetic field of suitable intensity that is applied from outside and, after the outside field is turned off, the relaxation of the magnetization of the magnetic markers is measured with the aid of magnetic field sensors, whereby the different relaxation behaviors of the magnetic markers bound with the analyte relative to the unbound magnetic markers are used for analysis.

As a measurement variable, the complex susceptibility of the samples can also be determined as a function of frequency.

Also in this case, it is possible to combine the analytes to be identified, instead of structure-specific substances, with the magnetic labelings.

Structure-specific substances are defined as all substances that bind specifically to certain structures. Structure-specific substances are defined as especially antibodies, antibody fragments, biotin, or substances that bind biotin such as avidin and streptavidin, agonists that bind specifically to receptors, such as cytokines, lymphokines, endothelins or their antagonists, specific peptides and proteins, receptors, enzymes, enzyme substrates, nucleotides, ribonucleic acids, deoxyribonucleic acids, carbohydrates, lipoproteins, etc. As structure-specific substances, substances are preferred whose binding constant is in the range of $10^5$–$10^{15}$ $(mol/l)^{-1}$. Especially preferred are substances whose binding constant is in the range of $10^7$–$10^{15}$ $(mol/l)^{-1}$.

The structure-specific substances or analytes to be identified can be labeled with the ferrimagnetic or ferromagnetic particles with the aid of processes that are familiar in immunochemistry, peptide chemistry, and protein chemistry. Especially advantageous are covalent bonds between the structure-specific substances or the analytes to be identified with the substances that form the stabilizing shell of ferrimagnetic or ferromagnetic particles. Examples of especially suitable methods are activation and coupling with the aid of carbodiimides (Jakoby and Wilchek, eds., 1974 Methods Enzymol. 34), the formation of Schiff bases after periodates are exposed to compounds that contain carbohydrates (Wicheck and Bayer, eds., Methods Enzym. 184:177), which are then optionally reduced for further stabilization, coupling with the aid of glutaric dialdehyde (Heitzmann and Richards, 1974 Proc. Natl. Acad. Sci. USA 71:3537), cross-linking of bromoacetylated particles with thiolylated substances (Angerer et al., 1976 Cell 9:81), as well as reductive alkylation (Bayer et al., 1976 J. Histochem. Cytochem. 24:933).

Ferromagnetic or ferrimagnetic colloidal particles can also be produced with a stabilizing shell made of the structure-specific substance or the analyte to be identified, by the particles being put after production directly into a solution of the structure-specific substance, optionally in the presence of other adjuvants, such as, e.g., proteins, carbohydrates, as well as natural, synthetic, or partially synthetic surface-active substances, etc., or by being produced directly in the presence of structure-specific substances.

The process according to the invention can be used in, e.g., fertility, histocompatibility, allergology, infectiology, hygiene, genetics, virology, bacteriology, toxicology, pathology, environmental analysis, and medical diagnosis.

Also objects of this invention are compounds for magnet-relaxometric detection, which consist of colloidal suspensions of freely movable ferrimagnetic or ferromagnetic particles and structure-specific substances or analytes to be identified, whereby structure-specific substances are defined as especially antibodies, antibody fragments, biotin, or substances that bind biotin such as avidin and streptavidin, agonists that bind specifically to receptors, such as cytokines, lymphokines, endothelins or their antagonists, other specific peptides and proteins, receptors, enzymes, enzyme substrates, nucleotides, ribonucleic acids, deoxyribonucleic acids, carbohydrates, lipoproteins, etc.

The compounds for magnet-relaxometric detection can also consist of combinations of several ferromagnetic or ferrimagnetic particles with relaxation times that can be discriminated, since measurement results that can be discriminated individually can be achieved through the use of different magnetic labelings with respectively a very narrow distribution of relaxation times and/or magnetic moments for various structure-specific substances or analytes inside a sample. As a result, direct simultaneous quantitative determination of several analytes is made possible.

As suspension media, all liquids in which the colloidal particles can move freely are suitable. Especially suitable are water, aqueous solutions of surface-active adjuvants, such as, e.g., surfactants or oligomeric or polymeric carbohydrates and proteins, as well as mixtures of water and alcohols such as, e.g., glycerol and polyethylene glycol. The suspension media can additionally contain adjuvants that change the osmotic pressure, such as, e.g., common salt. In addition, buffer substances that determine pH, such as, e.g., phosphates, can be contained.

The compounds made of ferromagnetic or ferrimagnetic colloidal particles with structure-specific substances or analytes to be identified can also be present in dried form, optionally in combination with other adjuvants which, e.g., facilitate drying or increase the stability of the dried product (e.g., as lyophilizates).

Finding of the analyte can be done with or without separation and washing steps. In carrying out measurements with separation steps between bound and unbound magnetic markers, all ferromagnetic or ferrimagnetic colloidal substances according to the invention can be used as magnetic labelings for magnetrelaxometric detection. In these cases, special requirements with regard to the Brownian relaxation times and the Néelian relaxation times no longer need be imposed.

Due to the binding identification based on physical mechanisms, non-specific measurement signals (matrix phenomena) can be largely ruled out. The specificity of the process thus depends only on the "true" specificity of the structure-specific substance (cross reactivity of antibodies, non-specific binding of ligands).

Due to the high sensitivity of the process according to the invention, it is easy to remain under the detection limits of binding assays that are otherwise commonly encountered.

As substances for magnetic labeling, all ferromagnetic or ferrimagnetic materials that can be dispersed colloidally in a medium that is suitable for magnetorelaxometric detection can be used. When using substances for magnetorelaxometric detection, which is carried out without separation steps between bound and unbound magnetic markers, the Néelian relaxation time of the magnetic labelings under the measurement conditions must be longer than the Brownian relaxation time of the magnetic markers. Especially suitable are all ferromagnetic or ferrimagnetic colloidal particles with Brownian relaxation times in aqueous media in the range of $10^{-8}$–$10^{-1}$ s and Néelian relaxation times of more than $10^{-8}$ s. To carry out measurements without separation steps, the viscosity of the dispersing medium used must be matched to the relaxation times of the ferromagnetic and ferrimagnetic particles and the measurement time since the suspension medium basically determines the time constant of Brownian relaxation.

Preferred are especially ferromagnetic or ferrimagnetic colloidal particles made of iron, iron oxides, barium ferrites, strontium ferrites, cobalt, nickel, nickel ferrites, cobalt ferrites, and chromium dioxide, whose Néelian relaxation time is longer than the Brownian relaxation time.

The use of magnetic labelings with narrowly distributed particle sizes and/or magnetic moments is generally advantageous. Separation of magnetic labelings into fractions with a narrow distribution of particle sizes can be achieved by, e.g., chromatographic processes or by using special filtration processes (e.g., glass capillary systems or tangential filtration), by using molecular sieves, or by means of centrifuging. Magnetic labelings with moments that are as uniform as possible can be produced, e.g., by classification in a magnetic gradient field.

The ferromagnetic and ferrimagnetic substances can be stabilized with a shell made of oligomeric or polymeric carbohydrates, proteins, peptides, nucleotides, surfactants, other monomers, oligomers, or polymers and/or lipids.

The particle sizes of the ferromagnetic and ferrimagnetic substances are advantageously between 1 nm and 400 nm. Especially preferred are particle sizes between 1 nm and 100 nm.

According to the process, the magnet-relaxometric detection is carried out with measurement arrangements that first make it possible to magnetize the sample to be studied with the aid of a suitable magnetic field and then to measure the magnetic relaxation of the magnetic markers. The measurement arrangement used for the examples is depicted in FIG. 2. In contrast to all other already known processes (JP-235774 and WO 91/15243), in the measurement of the relaxation of magnetization in the process according to the invention, it is not static magnetization in the presence of the magnetizing field that is measured but rather its time change in the absence of the magnetizing field. Only thus are data on the binding state of the markers available. In addition, influencing of the measurement signal by diamagnetic or paramagnetic components or contaminants is thus avoided. Further, measurement sensitivity is increased decisively.

It is further possible to carry out the measurement of the frequency-dependent magnetization of the marker because of a suitable alternating magnetic field (determination of complex susceptibility as a function of frequency) with the aid of highly sensitive sensors, such as, for example, SQUIDs, in the presence of the field. In this case, use is made of the specific frequency dependence of the susceptibility of the magnetic marker, in contrast to the frequency dependence of the paramagnetic or diamagnetic components that can be determined separately. Also, this procedure differs from the process for determining the susceptibility of superparamagnetic substances that is proposed in WO91/15243. In WO91/15243, neither the frequency dependency of the susceptibility of the magnetic markers is described, nor is a process for using this property indicated.

Below, processes are described that make it possible to detect in vivo the retention site and the extent of the specifically bound markers without being influenced by markers that circulate in the blood. In addition, in these processes, the use of radioactive substances, as has been required thus far in carrying out scintigraphy processes, is avoided.

The processes according to the invention are based on the fact that the relaxation time differences between bound and unbound magnetic markers in liquids, as well as the change of the predominant relaxation mechanism by binding the magnetic markers to solid phases, can also be used for magnet-relaxometric detection of substances or structures in vivo. Such processes are also referred to below as immune magnetography or immunomagnetography.

The in vivo measurement of the spatial distribution of a relaxing magnetic markers that are used in humans in the time range of the measurement can be carried out by two different measuring methods:

1. Production of as homogeneous a magnetic field as possible in advantageous volume, turning off the field and measuring the spatial distribution of the relaxing magnetic field with the aid of a multichannel sensor. Said sensor should enclose the measurement object as completely as possible. For the production of sufficient measurement information, repeated measurement with sequential rastering of the measurement object is also possible.
2. Sequential production of a local field that is limited in space, turning off the field and measuring the spatial distribution of the relaxing magnetic field with the aid of a single-channel sensor. The use of a multichannel sensor is also possible.

In the case of both methods, to obtain as many data as possible both the magnetization of the measurement object and the measuring of the resulting magnetic field in all three spatial directions are to be preferred.

The measurement is described by a suitable model. Preferably, the model of the magnetic dipole, multipole or multi-dipole is used as a basis. The special parameters of the model, especially the sites of the dipoles or multipoles, are found by a suitable approximation process, which minimizes the deviations between measurement data and model parameters. These parameters provide information on the spatial distribution of the magnetized particles.

An analogous approach is known and proven for the analysis of magnetic fields of bioelectric currents.

As processes and compounds that are suitable for immune magnetography, all processes and substances that are cited for magnet-relaxometric detection can be used.

Especially suitable for carrying out immune magnetography are magnetic labelings, which are biodegradable and compatible. This is especially true of magnetic labelings, which consist of iron oxides.

To carry out binding-specific magnet-relaxometric detection in vivo, it is necessary that the Brownian relaxation times of the combinations, introduced in the human body, of ferrimagnetic or ferromagnetic substances with structure-specific substances at body temperature in bodily fluids be shorter than the Néelian relaxation times.

In immune magnetography, structure-specific substances are defined especially as all substances that bind specifically to structures of the human body to be identified. Especially suitable are antibodies, antibody fragments, agonists that bind specifically to receptors or their antagonists, specific peptides and proteins, receptors, enzymes, enzyme substrates, nucleotides, ribonucleic acids, deoxyribonucleic acids, carbohydrates, or lipoproteins. Among the agonists that bind to receptors, especially cytokines, lymphokines, or endothelins are suitable.

Well suited are all structure-specific substances that have a binding constant in the range of $10^5$–$10^{15}$ (mol/l)$^{-1}$. Especially suitable are all structure-specific substances that have a binding constant in the range of $10^7$–$10^{15}$ (mol/l)$^{-1}$.

The following examples explain the invention without limiting it.

Embodiment 1

100·g of a monoclonal antibody to collagen III, referred to below as anticollagen III, is dissolved in 500·l of 0.1 M sodium bicarbonate solution. 1 ml of dextran-coated magnetite suspension with 1 mol of Fe/l and a particle size of about 40 nm is buffered via a Sephadex column (Pharmacia PD 10) with 0.1 M sodium bicarbonate. 0.5 ml of 10 mmol of sodium periodate solution is added to the suspension. The solution is allowed to stand in the dark for 2 hours. Then, it is eluted via a PD 10 with 0.1 M sodium bicarbonate solution. The anticollagen III solution is added to the suspension. The mixture is allowed to stand in the dark for 3 hours at 4° C. Then, 5 mg of NaBH$_4$ is added as a solid and briefly swirled. The mixture is allowed to stand in the dark for 8 hours at 4° C. Then, the magnetite-labeled anticollagen III (referred to below as mag-anticollagen III) is eluted via a PD 10 column with phosphate-buffered common salt solution (PBS, pH 7.4).

A solution of 5·g of collagen III in 200·l of buffer (phosphate-buffered common salt solution (PBS)) is incubated in a polystyrene sampling vessel. Then, the liquid phase is discarded. The sampling vessel is flushed three times with phosphate-buffered common salt solution, containing 0.1% Tween 20 (PBST). 5·l of mag-anticollagen III in 200·l of PBST is added to the sample. It is incubated for 1 hour at room temperature. Then, the sample is magnetized in a magnetically shielded chamber in a field with an intensity of 2 mT 4 cm below the squid detector (see FIG. 2). 400 ms after the magnetic field is turned off, the relaxation measurement is carried out over 100 s. In the sample, relaxation is identified from a diminishing field (see FIG. 3).

Embodiment 2

A solution of 5·g of collagen V in 200·l of PBS buffer of pH 7.4 is incubated in a sampling vessel made of polystyrene. Then, the liquid phase is discarded. The sampling vessel is flushed three times with PBST washing buffer of pH 7.4. 5·l of mag-anticollagen III, produced according to Example 1, in 200·l of PBST is added to the sample. It is incubated for 1 hour at room temperature. Then, the sample is magnetized in a magnetically shielded chamber in a field with an intensity of 2 mT 4 cm below the SQUID detector (see FIG. 2). After the magnetizing field is turned off, the sample is measured. 400 ms after the magnetic field is turned off, the relaxation measurement is carried out over 100 s. In the sample that contains collagen V, no diminishing magnetic field can be detected within the limits of measurement reliability (see FIG. 4).

Embodiment 3

100·l of glutaric dialdehyde (3% in water) is added to a solution of 100·g of collagen III in 1 ml of PBS. The solution is stirred for 24 hours at 4° C. and then centrifuged off. The pellet contains precipitated crosslinked collagen III. The crosslinked collagen III is suspended in 1 ml of PBS. (Sample 1). 100·l of glutaric dialdehyde solution (3% in water) is added to a solution of 100·g of collagen V in 1 ml of PBS. The solution is stirred for 24 hours at 4° C. and then centrifuged off. The pellet contains precipitated crosslinked collagen V. The crosslinked collagen V is suspended in 1 ml of PBS. (Sample 2). 5·l each of mag-anticollagen III suspension of Example 1 is added to samples 1 and 2. It is incubated for 1 hour at 37° C. Then, both samples are magnetized in a shielded chamber in a magnetic field with an intensity of 2 mT via a SQUID detector. 400 ms after the magnetizing field is turned off, the relaxation measurement is carried out. In the case of sample 1, a diminishing field is measured. In the case of sample 2, no diminishing field can be detected.

Embodiment 4

From 10 ml of a 1.9 mg/ml collagen III solution in PBS (pH 7.4), 5 ml each of the following dilutions is produced: 10,000 ng/ml, 1,000 ng/ml, 100 ng/ml, 10 ng/ml, 1 ng/ml Three times 1 ml each is pipetted from each dilution into polystyrene tubes (2.5 ml capacity). It is inhibited for 1 hour at 37° C. Then, the contents of the tubes are discarded. The tubes are washed three times with 1 ml of PBST each.

1 ml of a 1:100 dilution of the magnetite-labeled antibody, produced according to Example 1, is added to each tube. The tubes are allowed to stand for 1 hour at room temperature. Then, the samples are magnetized (2 mT) with the measuring arrangement outlined in FIG. 2 and, after the magnetizing field is turned off, the relaxation is measured over 100 s. The evaluation of the differences of the measured magnetic flux densities 200 ms and 100 s after the magnetizing field is turned off yields the relationship shown in FIG. 1.

Embodiment 5

100·g of a monoclonal antibody to collagen III, referred to below as anticollagen III, is dissolved in 500·l of 0.1 M sodium bicarbonate solution. 1 ml of dextran-coated magnetite suspension with 1 mol of Fe/l and a particle size of about 40 nm is buffered via a Sephadex column (Pharmacia PD 10) with 0.1 M sodium bicarbonate. 0.5 ml of 10 mmol of sodium periodate solution is added to the suspension. The solution is allowed to stand in the dark for 2 hours. Then, it is eluted via a PD 10 with 0.1 M of sodium bicarbonate solution. The anticollagen III solution is added to the suspension. The mixture is allowed to stand in the dark for 3 hours at 4° C. Then, 5 mg of NaBH$_4$ is added as a solid and briefly swirled. The mixture is allowed to stand in the dark for 8 hours at 4° C. Then, the magnetite-labeled anticollagen III (referred to below as mag-anticollagen III) is eluted via a PD 10 column with phosphate-buffered common salt solution (PBS, pH 7.4).

20·l each of the mag-anticollagen III suspension is diluted with 39·l of phosphate-buffered common salt solution of pH 7.4, which in addition contains 0.1% PBST, and is filled in three sampling vessels made of polyacrylic acid, which in each case have a capacity of 500·l. 100·l of an aqueous solution of human serum albumin (1 mg of albumin/ml) is added to the first sampling vessel (sample 1). 100·l of a solution of collagen V in PBST (1·g of collagen V/ml) is added to the second sampling vessel (sample 2). 100·l of a solution of collagen III in PBST (1·g of collagen III/ml) is added to the third sampling vessel (sample 3). 200 s after the protein solutions are added, the samples are magnetized (2 mT) with the measuring arrangement outlined in FIG. 2, and 20 ms after the magnetizing field is turned off, the magnetic relaxation is determined beginning with 1 s in each case. In samples 1 and 2, no diminishing magnetic field can be detected within the limits of measurement reliability. In sample 3, however, a diminishing magnetic field can be detected. After the sampling vessels are emptied and flushed three times with 500·l of PBST each, the measurements are repeated. A diminishing magnetic field can now be detected in none of the sampling vessels within the limits of measurement reliability.

Embodiment 6

100·g of avidin is dissolved in 500·l of 0.1 M sodium bicarbonate solution. 1 ml of dextran-coated magnetite suspension with 1 mol of Fe/l and a particle size of about 40 nm is buffered via a Sephadex column (Pharmacia PD 10) with 0.1 M sodium bicarbonate. 0.5 ml of 10 mmol of sodium periodate solution is added to the suspension. The solution is allowed to stand in the dark for 2 hours. Then, it is eluted via a PD 10 with 0.1 M sodium bicarbonate solution. The avidin solution is added to the suspension. The mixture is allowed to stand in the dark for 3 hours at 4° C. Then, 5 mg of $NaBH_4$ is added as a solid and briefly swirled. The mixture is allowed to stand in the dark for 8 hours at 4° C. Then, the magnetite-labeled avidin (referred to below as mag-avidin) is eluted via a PD 10 column with phosphate-buffered common salt solution (PBS, pH 7.4).

1 mg of bovine serum albumin is conjugated with biotin-NHS (referred to below as biotin albumin) and diluted to a concentration of 1 ·g/ml in PBS. 1 ml of the biotin-albumin dilution is incubated for 3 hours at room temperature in a polystyrene sampling vessel. Then, the liquid phase is discarded. The sampling vessel is flushed three times with phosphate-buffered common salt solution, containing 0.1% Tween 20 (PBST). 5·1 of mag-avidin is added to the sample. It is incubated for 1 hour at room temperature. Then, the sample is magnetized in a magnetically shielded chamber in a field with an intensity of 2 mT 4 cm below the squid detector (see FIG. 2). 400 ms after the magnetic field is turned off, the relaxation measurement is carried out over 100 s. In the sample, a diminishing magnetic field is measured.

1 ml of a dilution of bovine serum albumin in PBS (0.1 is incubated for 3 hours at room temperature in a sampling made of polystyrene. Then, the liquid phase is discarded. The sampling vessel is flushed three times with phosphate-buffered common salt solution, containing 0.1% Tween 20 (PBST). 5·1 of mag-avidin is added to the sample. It is incubated for 1 hour at room temperature. Then, the sample is magnetized in a magnetically shielded chamber in a field with an intensity of 10 mT 4 cm below the squid detector (see FIG. 2). 400 ms after the magnetic field is turned off, the relaxation measurement is carried out over 100 s. In the sample, no diminishing magnetic field is measured within the limits of measurement reliability.

Figure 1:
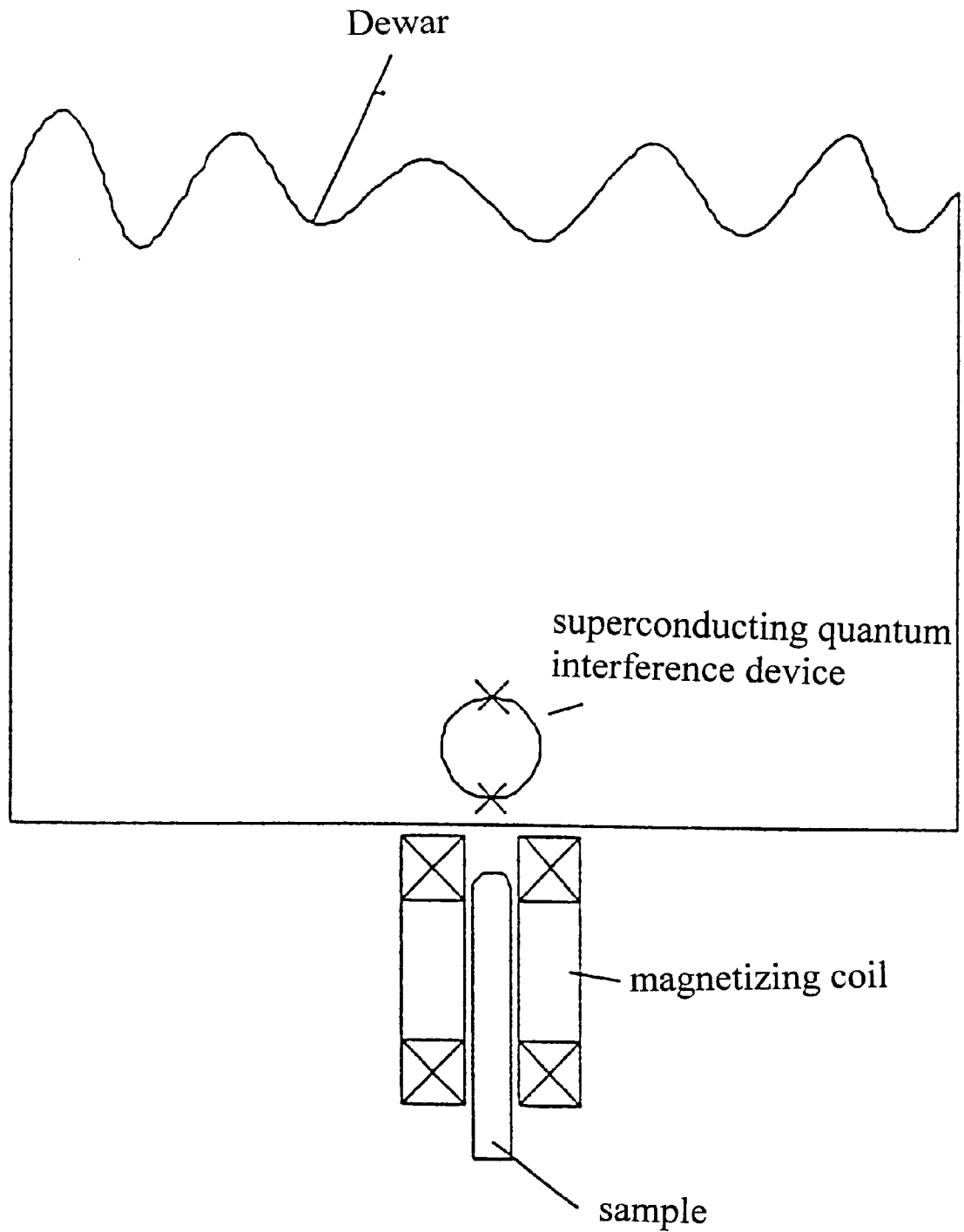
FIG. 1 shows the differences of magnetic flux density B as a function of the collagen concentration in the sample.
Figure 2:
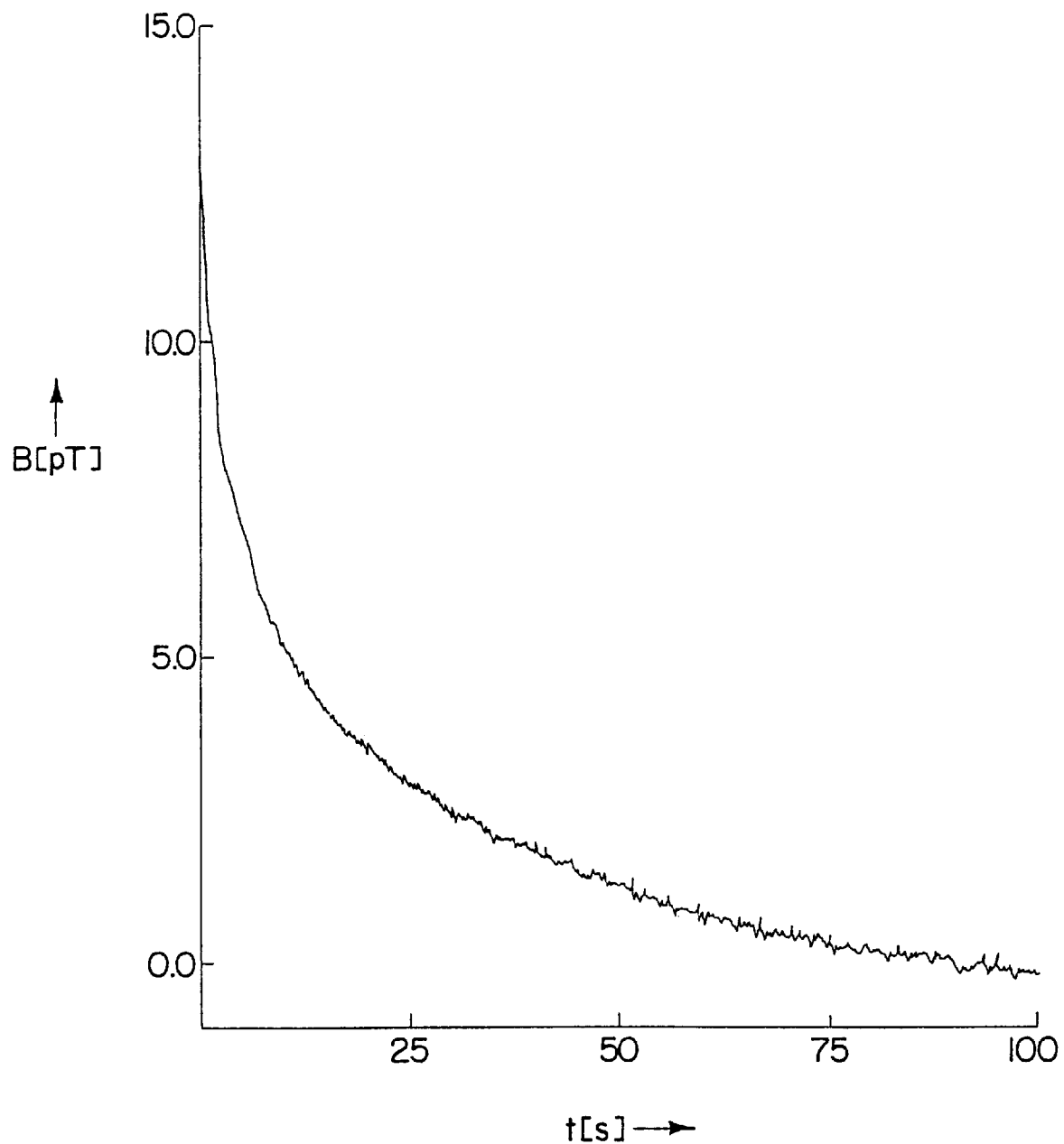
FIG. 2 shows the measuring arrangement for the magnet-relaxometric detection of analytes
Figure 3:
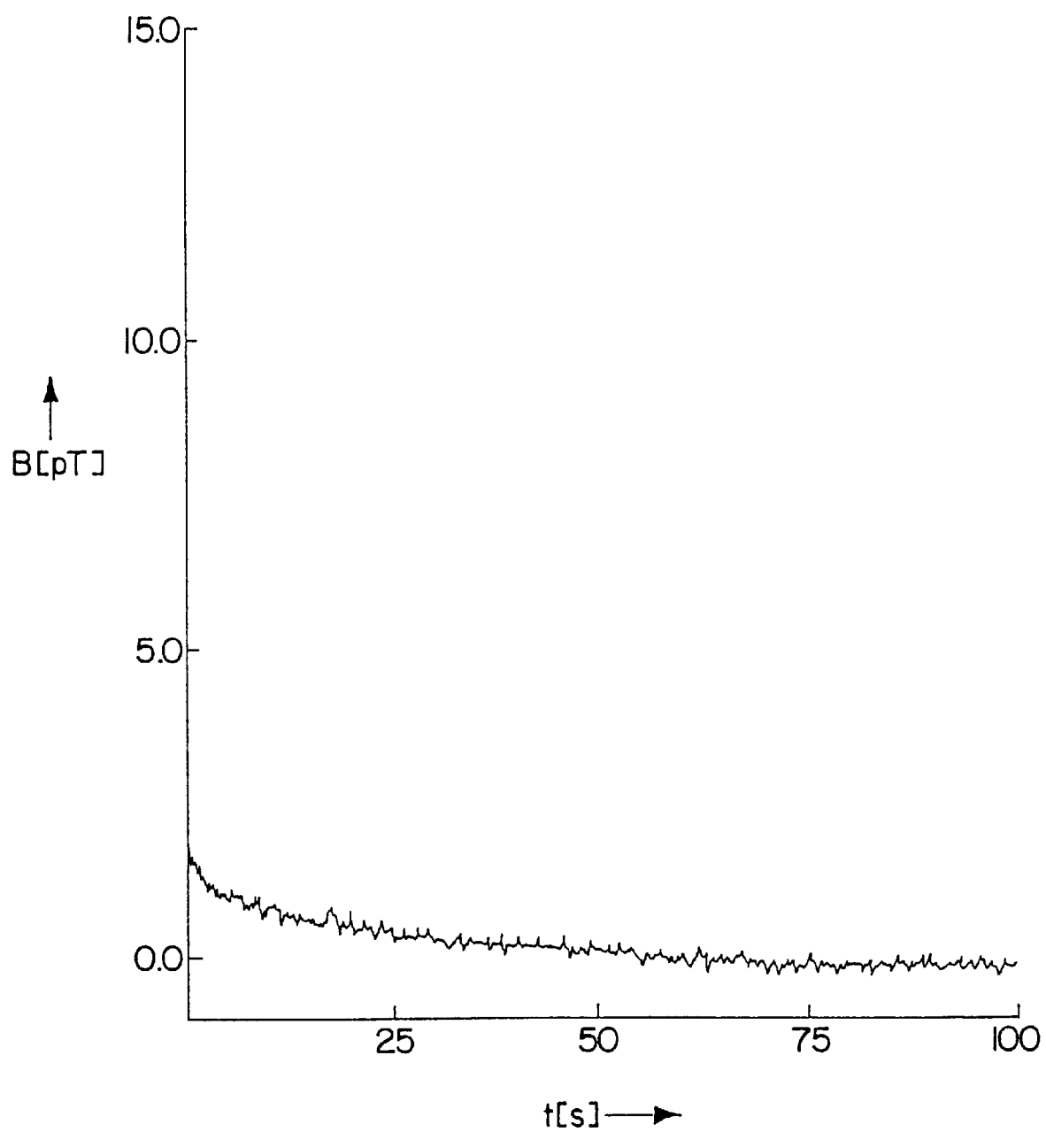
FIG. 3 shows the relaxation signal of the sample that contains collagen III
Figure 4:
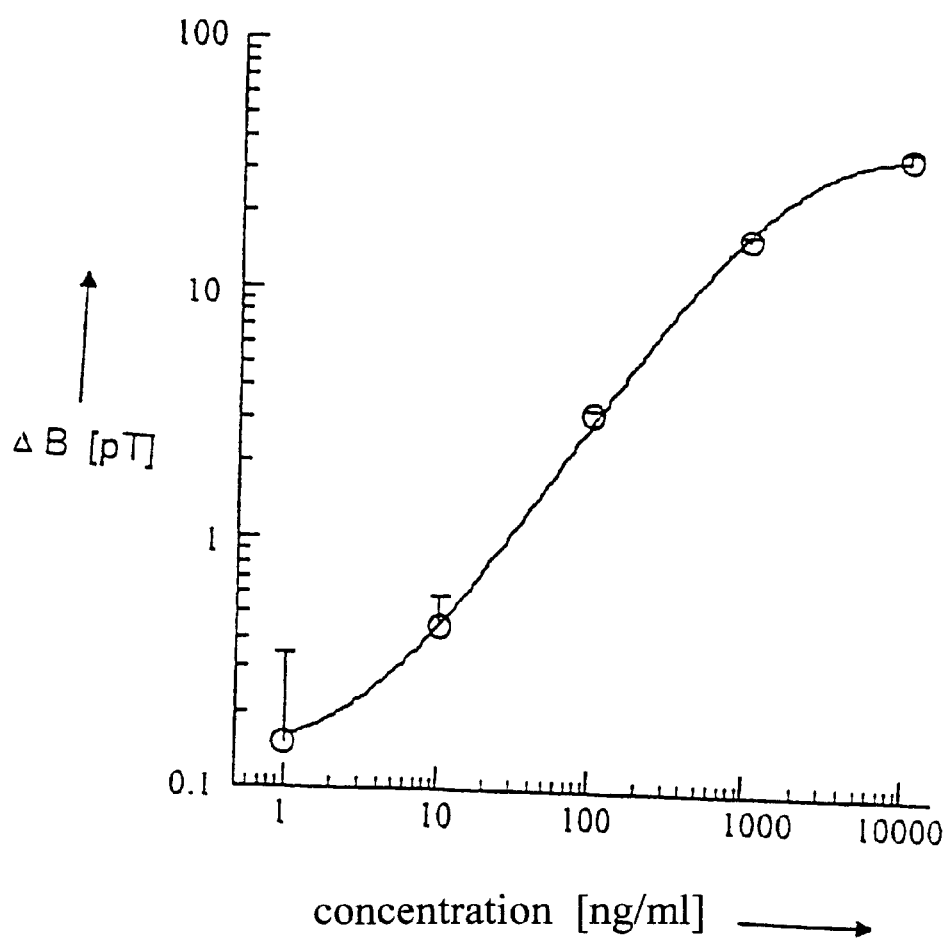
FIG. 4 shows the relaxation signal of the sample that contains collagen V

What is claimed is:
1. A method of detection of an analyte in liquid phase in a fertility process, histocompatability process, allergology process, infectiology process, hygiene process, genetics process, virology process, bacteriology process, toxicology process, pathology process, environmental analysis process, or medical diagnosis process, comprising
(i) adding ferromagnetic or ferrimagnetic colloidal particles which bind an analyte directly or bind a structure specific substance which is bound to an analyte,
(ii) magnetizing the ferromagnetic or ferrimagnetic colloidal particles in a magnetic field,
(iii) measuring the relaxation of the particles when the magnetic field is turned off, and
(iv) correlating the degree of relaxation of said particles with the concentration of analyte
wherein the colloidal particles have a Brownian relaxation under measurement conditions shorter than their Néelian relaxation.

2. A method according to claim 1, wherein the ferromagnetic and ferrimagnetic substances have a particle size in the range of 1 to 400 nm.

3. A method according to claim 1, wherein the ferromagnetic and ferrimagnetic particles have a particle size of 1 to 100 nm.

4. A method according to claim 1, wherein the ferromagnetic and ferrimagnetic particles are stabilized with a shell made of oligomer of polymeric carbohydrates, proteins, peptides, nucleotides, surfactants, polymers, and/or lipids.

5. A method according to claim 1, wherein the structure-specific substances are antibodies, antibody fragments, biotin, substances that bind biotin, agonists that bind specifically to receptors or their antagonists, peptides, proteins, receptors, enzymes, enzyme substrates, nucleotides, ribonucleic acids, deoxyribonucleic acids, carbohydrates, or lipoproteins.

6. A process according to claim 1, wherein the structure-specific substances have a binding constant in the range of $10^7$–$10^{15}$ $(mol/l)^{-1}$.

7. A method according to claim 1, wherein the ferrimagnetic or ferromagnetic substances are iron oxides.

8. A method of detection according to claim 1, comprising a medical diagnosis process performed on a human.

9. A method of detection according to claim 1, performed on a human.

10. A method of detection according to claim 1, comprising measuring magnetic relaxation in a host having been administered the analyte.

11. A method according to claim 10, wherein the host is a human.

12. The method according to claim 1, wherein the relaxation is measured with magnetic field sensors, which are superconducting quantum interference devices (SQUIDS), induction coils, flux gate magnetometers, giant magnetoresistance sensors, or magnetoresistance converters.

* * * * *

UNITED STATES PATENT AND TRADEMARK OFFICE
CERTIFICATE OF CORRECTION

PATENT NO. : 6,485,985 B1
DATED : November 26, 2002
INVENTOR(S) : Werner Weitschies et al.

It is certified that error appears in the above-identified patent and that said Letters Patent is hereby corrected as shown below:

Title page,
Item [75], Inventors, "Kottiz" should read -- Kotitz --; and "Lucz" should read
-- Lutz --
After Item [63], Related U.S. Application Data, insert Item:

-- [30]    Foreign Application Priority Data

01/27/95      (DE)............... 19503664 --

Column 12,
Line 23, "oligomer of polymetric" should read -- oligomeric or polymeric --

Signed and Sealed this

Seventh Day of December, 2004

JON W. DUDAS
*Director of the United States Patent and Trademark Office*